United States Patent [19]
DiGiacomo et al.

[11] 4,298,723
[45] Nov. 3, 1981

[54] LAYERED OR AMORPHOUS ACYCLIC ORGANOMETALLIC INORGANIC POLYMERS

[75] Inventors: Peter M. DiGiacomo, Mission Viejo; Martin B. Dines, Santa Ana, both of Calif.

[73] Assignee: Occidental Research Corporation, Irvine, Calif.

[21] Appl. No.: 78,625

[22] Filed: Sep. 25, 1979

Related U.S. Application Data

[63] Continuation-in-part of Ser. No. 945,971, Sep. 26, 1978, Pat. No. 4,232,146, and Ser. No. 60,079, Jul. 24, 1979.

[51] Int. Cl.³ .................. C08G 79/00; C08G 79/04
[52] U.S. Cl. .................. 528/271; 260/429.1; 260/429.2; 260/429.3; 260/429 R; 260/429.5; 260/435 R; 528/9; 528/362; 528/374; 528/391; 528/395
[58] Field of Search .......... 528/9, 395, 362, 271, 528/374, 391; 260/429 R, 429.1, 429.3, 429.5

[56] References Cited

U.S. PATENT DOCUMENTS

| | | | |
|---|---|---|---|
| 3,231,347 | 1/1966 | Revukas | 44/68 |
| 3,445,492 | 5/1969 | Washburn et al. | 260/429 R |
| 3,491,133 | 1/1970 | Revukas | 260/438 |
| 3,615,807 | 10/1971 | Yates | 106/299 |
| 3,634,479 | 1/1972 | Ridenour | 528/9 |
| 3,654,189 | 4/1972 | Venczky | 260/33.8 R |
| 3,663,460 | 5/1972 | Block et al. | 260/33.6 R |

FOREIGN PATENT DOCUMENTS 2614356 10/1977 Fed. Rep. of Germany .
539293 9/1941 United Kingdom .
1406419 9/1975 United Kingdom .

OTHER PUBLICATIONS

Chem. Abstract 83, 70750g (1975).
Chem. Abstract 85, 13433y (1976).
Chem. Abstract 86, 155758c (1977).
Chem. Abstract 58, 1487b (1963).
Chem. Abstract 55, 11161c (1961).
Orlov & Vorankof (1965).
Dub, "Organometallic Compounds," Springer-Verlog, Berlin VIII, pp. 187-191 (1962).
Doak et al., "Organometallic Compounds of Arsenic, Antimony and Bismuth," Wiley, Intersc., N.Y. pp. 46-49 (1970).

Primary Examiner—Wilbert J. Briggs, Sr.
Attorney, Agent, or Firm—Christie, Parker & Hale

[57] ABSTRACT

Inorganic compounds which contain pendant organic functional groups are prepared by the reaction of an acid of the formula $[(HO)_2OZO_x]_kR$, in which Z is a pentavalent metal, X is 0 or 1, k is 1 or 2, and R is an acyclic organo group, with a tetravalent metal ion. The compounds are insoluble in the reaction medium, exist in a layered crystalline to amorphous form, and have the formula $M(O_3ZO_xR)_n$, in which M is the tetravalent metal and n is 1 or 2. One use for the compounds is as selective sorbents.

28 Claims, 17 Drawing Figures

SEMI CRYSTALLINE
$Zr(O_3PCH_2CH_2CO_2H)_2$

Fig. 8

HIGHLY CRYSTALLINE
$Zr(O_3PCH_2CH_2CO_2H)_2$

LAYERED OR AMORPHOUS ACYCLIC ORGANOMETALLIC INORGANIC POLYMERS

CROSS-REFERENCE TO RELATED APPLICATIONS

This application is a continuation-in-part of copending applications Ser. No. 945,971, filed Sept. 26, 1978 now U.S. Pat. No. 4,232,146 issued Nov. 4, 1980, and Ser. No. 060,079, filed July 24, 1979 (and titled "Layered Organophosphorus Inorganic Polymers Containing Acyclic Groups"), and is related to the following applications:

| Serial No. | Filing Date | U.S. Pat. No. |
| --- | --- | --- |
| 952,228 | October 17, 1978 | 4,235,990 |
| 966,197 | December 4, 1978 | 4,235,991 |
| 007,275 | January 29, 1979 | |
| 043,810 | May 30, 1979 | |
| 054,107 | July 2, 1979 | |
| 054,097 | July 2, 1979 | |
| 060,076 | July 24, 1979 | |
| 060,250 | July 24, 1979 | |
| 060,249 | July 24, 1979 | |
| 060,078 | July 24, 1979 | |
| 060,077 | July 24, 1979 | | and to the application titled "Layered or Amorphous Cyclic Organometallic Inorganic Polymers", Ser. No. 78,636 filed concurrently herewith on Sept. 25, 1979. The disclosure of each application noted above is hereby incorporated herein by reference.

BACKGROUND OF THE INVENTION

The present invention is directed to solid inorganic polymers having organo groups anchored to the surfaces of the polymers. The majority of the polymers formed are layered crystals which display intercalation activity.

The interface surfaces of solids, whether amorphous, crystalline, or semicrystalline, are responsive regions of chemical and physical action. In many practical chemical and physical phenomena, such as absorption, corrosion inhibition, heterogeneous catalysis, lubrication, ion exchange activity, adhesion and wetting and electrochemistry, activity occurs as a consequence of the presence of a definable solid surface.

Figure 1:
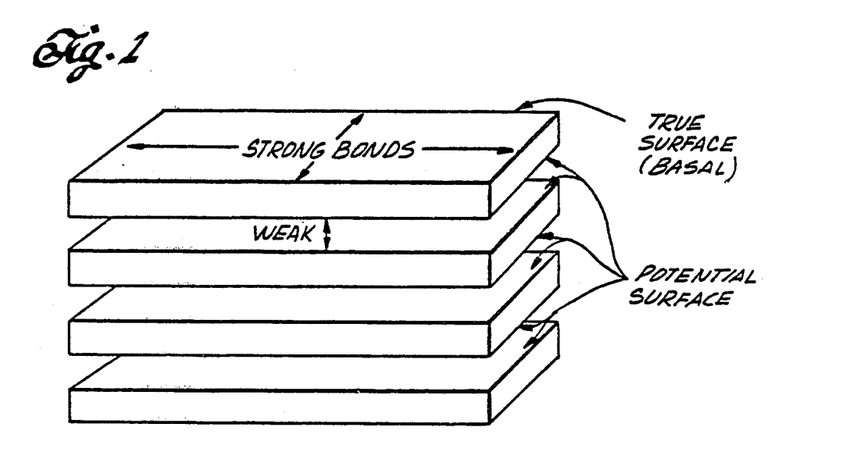
FIG. 1 illustrates a layered microcrystal. Each lamellar slab is formed of strong covalent bonds and has a thickness of about 10 atoms.

Many inorganic solids crystallize with a layered structure and some could present sites for anchoring active groups. In this form, sheets or slabs with a thickness of from one to more than seven atomic diameters lie upon one another. With reference to FIG. 1, strong ionic or covalent bonds characterize the intrasheet structure, while relatively weak van der Waals or hydrogen bonding occurs between the interlamellar basal surfaces in the direction perpendicular to their planes. Some of the better known examples are prototypal graphite, most clay minerals, and many metal halides and sulfides. A useful characteristic of such materials is the tendency to incorporate "guest" species in between the lamella.

Figure 2:
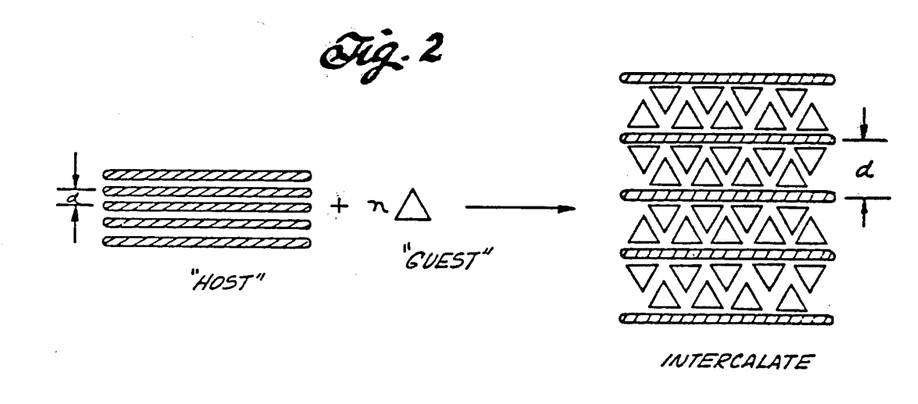
FIG. 2 illustrates intercalation where the interlayer distance is shown as "d."

In this process, designated, "intercalation," the incoming guest molecules, as illustrated in FIG. 2, cleave the layers apart and occupy the region between them. The layers are left virtually intact since the crystals simply swell in one dimension, i.e., perpendicular to the layers. If the tendency to intercalate is great, then the host-layered crystal can be thought of as possessing an internal "super surface" in addition to its apparent surface. In fact, this potential surface will be greater than the actual surface by a factor of the number of lamella composing the crystal. This value is typically on the order of $10^2$ to $10^4$. Although edge surface is practically insignificant compared to basal surface, it is critical in the rate of intercalation, since the inclusion process always occurs via the edges. This is because bonding within the sheets is strong and, therefore, basal penetration of the sheets is an unlikely route into the crystal.

In graphite, the function of the host is essentially passive. That is, on intercalation, the host serves as the matrix or surface with which the incoming guest molecules interact, but throughout the process and on deintercalation the guests undergo only minor perturbation.

In order for a more active process to occur during intercalation, such as selective complexation of catalytic conversion, specific groups must be present which effect such activity.

An approach in which catalytically active agents have been intercalated into graphite or clays for subsequent conversions has been described in "Advanced Materials in Catalysis," Boersma, Academic Press, N.Y. (1977), Burton et al, editors, and "Catalysis in Organic Chemistry," Pinnavia, Academic Press, N.Y. (1977), G. V. Smith, editor.

Figure 3:
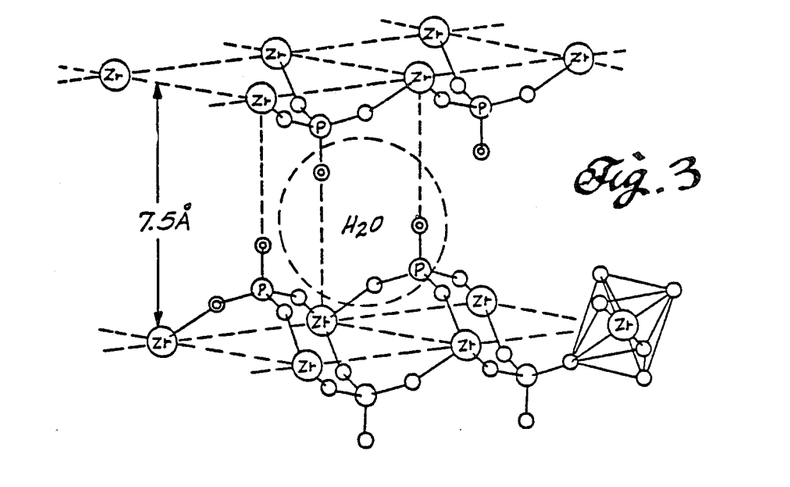
FIG. 3 illustrates the accepted structure for zirconium phosphate and spacing between layers. The dashed lines between zirconium (Zr) atoms is to establish the plane between them. In the drawing, P is phosphorus, O is oxygen and water of hydration is shown.

One of the few layered compounds which have potential available sites is zirconium phosphate, $Zr(O_3POH)_2$. It exists in both amorphous and crystalline forms which are known to be layered. In the layered structure, the site-site placement on the internal surfaces is about 5.3 Å, which leads to an estimated 25 Å area per site. This area can accomodate most of the functional groups desired to be attached to each site. The accepted structure, symbolized projection of a portion of a layer of this inorganic polymer and a representation of an edge view of two layers, are shown respectively in FIGS. 3, 4 and 5.

Besides the advantageous structural features of zirconium phosphate, the material is chemically and thermally stable, and nontoxic.

Quite a bit of work has been conducted on the zirconium phosphate, mainly because it has been found to be a promising inorganic cation exchanger for alkali, ammonium and actinide ions, Alberti, "Accounts of Chemistry Res." 11, 163, 1978. In addition, some limited work has been described on the reversible intercalation behavior of layered zirconium phosphate toward alcohols, acetone, dimethylformamide and amines, Yamaka and Koisuma, "Clay and Clay Minerals" 23, 477 (1975) and Michel and Weiss, "Z. Natur," 20, 1307 (1965). S. Yamaka described the reaction of this solid with ethylene oxide, which does not simply incorporate between the layers as do the other organics, but rather was found to irreversibly react with the acidic hydroxyls to form a covalent bonded product, Yamaka, "Inorg. Chem." 15, 2811, (1976). This product is composed of a bilayer of anchored ethanolic groups aimed into interlayers. The initial layer-layer repeat distance is expanded from about 7.5 Å to 15Å, consistent with the double layer of organics present. The overall consequence of this reaction is to convert inorganic acid hydroxyls to bound organic alkanol groups.

A very recently reported effort in the field is Alberti, et al., "J. Inorg. Nucl. Chem.," 40, 1113 (1978). A method similar to that of this invention for the preparation of zirconium bis(benzenephosphonate), zirconium bis(hydroxymethanephosphonate)monohydrate, and zirconium bis(monoethylphosphate) is described, with descriptions of the properties for these products.

Following the Alberti publication, a paper by Maya appeared in "Inorg. Nucl. Chem. Letters," 15, 207 (1979), describing the preparation, properties and utility as solid phases in reversed phase liquid chromatography for the compounds $Zr(O_3POC_4H_9)_2 \cdot H_2O$, $Zr(O_3POC_{12}H_{25})_2$ and $Zr(O_3POC_{14}H_{21})_2$.

All of the compositions described herein can be useful in gas phase, liquid phase, gas liquid, reversed phase, and bulk and thin layer chromatography. The compounds can also be useful as hosts and carriers for organic molecules and especially biologically active organic molecules. They are also useful as catalysts or as supports for catalysts. For example, they can be used in an analogous fashion to the compositions which are discussed by Bailar, "Heterogenizing Homogeneous Catalysts," *Catalysis Reviews—Sci. & Eng.*, 10(1) 17–35 (1974) and Hartley and Vezey, "Supported Transition Metal Complexes as Catalysts," *Advances in Organometallic Chemistry*, 15, 189–235 (1977).

SUMMARY OF THE INVENTION

The inorganic polymers of this invention have organo groups covalently bonded to pentavalent metal atoms including phosphorus (which sometimes hereinafter are referred to as "pentavalent metals"). The pentavalent metal atoms are, in turn, covalently bonded by an oxygen linkage to tetravalent metal atoms. When formed in a layered crystalline state, they provide the organo groups on all of the apparent and interlamellar surfaces.

For convenience herein, the description of the inorganic polymers will be described with regard to phosphorus and its selection as the pentavalent metal. However, it is to be understood that the other pentavalent metals can be used and the description with regard to phosphorus will generally also apply analogously to the other pentavalent metals, for example, such pentavalent metals can be phosphorus, arsenic antimony, vanadium, niobium and tantalum. With regard to selecting arsenic as the pentavalent metal, the general description herein of phosphorus is analogous because an arsine is analogous to a phosphine, an arsenate to a phosphate, an arsonate to a phosphonate, an arsinate to a phosphinate, an arsenic compound to a phosphorus compound, an arsenic compound to a phosphonic compound, an arsenic acid to phosphoric acid, and an arsenious acid to phosphorous acid.

The process of preparation comprises a liquid media reaction in which at least one organo-substituted pentavalent metal acid is reacted with at least one tetravalent metal ion. For example, an organophosphorus acid compound of the formula:

$((HO)_2OP)_nR$ wherein n is 1 or 2 and R is an organo group covalently coupled to the phosphorus atom, and wherein when n is 2, R contains at least two carbon atoms and is directly or indirectly coupled to phosphorus atoms through different carbon atoms whereby the two phosphorus atoms are separated by at least two carbon atoms, is reacted with at least one tetravalent metal ion. The molar ratio of phosphorus to the tetravalent metal is 2 to 1. Reaction preferably occurs in the presence of an excess of the phosphorus acid compound and the metal ion is provided as a compound soluble in the liquid media.

Where only one specie of an organophosphorus acid compound is provided as the reactant with the tetravalent metal compound, the end product will have the empirical formula $M(O_3PR)_2$. Phosphoric and/or phosphorous acid can also be present as reactive diluents to form part of the solid inorganic polymeric structure which is the product of the reaction.

The products formed are layered crystalline to amorphous in nature. For all products, the R groups can be directly useful or serve as intermediates for the addition or substitution of other functional groups. When the product is crystalline and n is 2, cross-linking between the interlamellar layers occurs.

The normal liquid media is water. However, organic solvents, particularly ethanol, can be employed where water will interfere with the desired reaction. Preferably, the solvent is the solvent in which the organophosphorus acid compound is prepared. Where the organophosphorus acid compound has a sufficiently low melting point, it can serve as the liquid media.

The metathesis reaction occurs at temperatures up to the boiling point of the liquid media at the pressures involved, typically from ambient to about 150° C. and more preferably from ambient to about 100° C. While formation of the solid inorganic polymer is almost instantaneous, the degree of crystallinity of the product can be increased by refluxing the reaction products for times from about 5 to 15 hours. Crystallinity is also improved by employing a sequestering agent for the tetravalent metal ion.

DETAILED DESCRIPTION

Figure 14:
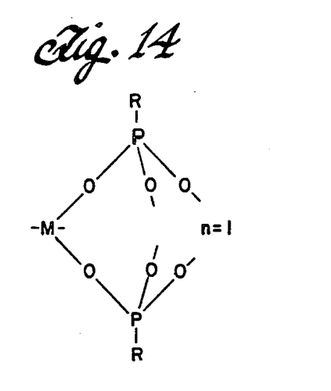
FIG. 14 shows the basic structural unit of the inorganic polymer wherein n is 1 and wherein P is phosphorus, O is oxygen, M is tetravalent metal and R is the organo group.
Figure 15:
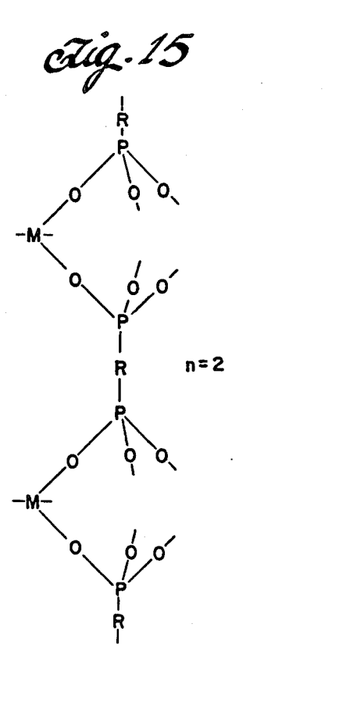
FIG. 15 shows the basic structural unit of the inorganic polymer wherein n is 2 and wherein P is a phosphorus atom, O is an oxygen atom, M is a tetravalent metal and R is the organo group.
Figure 16:
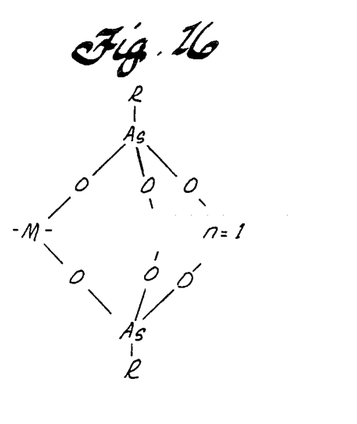
FIG. 16 shows the basic structural unit of an inorganic polymer wherein n is 1 and wherein As is arsenic (the pentavalent metal), O is oxygen, M is a tetravalent metal and R is the organo group.
Figure 17:
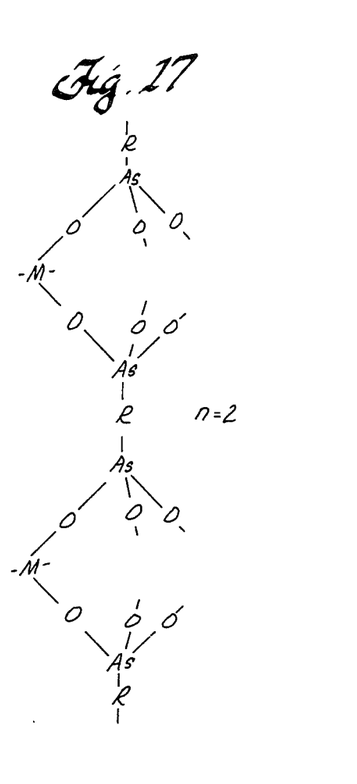
FIG. 17 shows the basic structural unit of an inorganic polymer wherein n is 2 and wherein As is arsenic, O is an oxygen atom, M is a tetravalent metal and R is the organo group.

According to the present invention there is provided inorganic polymers in layered crystalline to amorphous state formed by the liquid phase metathesis reaction of a tetravalent metal ion with an organo-substituted pentavalent metal acid, for example, at least one organophosphorus acid compound having the formula:

$$((HO)_2OP)_nR$$

wherein n is 1 or 2 and R is an organo group covalently coupled to the phosphorus atom to form a solid inorganic polymer precipitate in which the pentavalent metal (e.g., phosphorus) is linked to the tetravalent metal by oxygen and the organo group is covalently bonded to the pentavalent (e.g., phosphorus) atom. Illustrative with phosphorus in the organophosphorus compound wherein n is 2, the end product occurs in the bis configuration. In this configuration, R must contain two or more carbon atoms, preferably from two to about twenty carbon atoms, such that at least two carbon atoms separate the phosphorus atoms. In this bis configuration, no single carbon atom is bound directly or indirectly to more than one $(PO(OH)_2)$ group. When n is 1, and as depicted in FIGS. 14 and 16, the organo groups are pendant from phosphorus or arsenic atoms respectively. When n is 2, and as depicted in FIGS. 15 and 16, cross-linking occurs between interlamellar surfaces of the crystalline end product. Typically, the tetravalent metal ion is provided as a soluble salt $MX_4$ and X is the anion(s) of the salt. Typical anions include halides, $HSO_4^{-1}$, $SO_4^{-2}$, $O_2C-CH_3^{-1}$, $NO_3^{-1}$, $O^{-2}$ and the like.

Tetravalent metal ions useful herein are analogous to $Zr^{+4}$ in the process to make zirconium phosphate and phosphonate analogs and are metals with approximately the same ionic radius as $Zr^{+4}$ (0.8 Å); for example, the following:

| | | | | | | | |
|---|---|---|---|---|---|---|---|
| $Zr^{+4}$ | 0.80Å | $Te^{+4}$ | 0.81 | $Pr^{+4}$ | 0.94 | $Mn^{+4}$ | 0.5 |
| $W^{+4}$ | 0.66 | $Sn^{+4}$ | 0.71 | $Pb^{+4}$ | 0.92 | $Ir^{+4}$ | 0.66 |
| $U^{+4}$ | 0.89 | $Si^{+4}$ | 0.41 | $Os^{+4}$ | 0.67 | $Hf^{+4}$ | 0.81 |
| $Ti^{+4}$ | 0.68 | $Ru^{+4}$ | 0.65 | $Nb^{+4}$ | 0.67 | $Ge^{+4}$ | 0.53 |
| $Th^{+4}$ | 0.95 | $Pu^{+4}$ | 0.86 | $Mo^{+4}$ | 0.68 | $Ce^{+4}$ | 1.01 |

The majority of the polymeric reaction products formed from the above metals are found to be layered crystalline or semicrystalline in nature and, as such, provide layered structures similar to zirconium phosphates. The remainder are amorphous polymers possessing a large quantity of available pendant groups similar to silica gel.

By the term "organophosphorus acid compound," as used herein, there is meant a compound of the formula:

$$((HO)_2OP)_nR$$

wherein n is 1 or 2, R is any group which will replace a hydroxyl of phosphoric acid and/or the hydrogen of phosphorous acid and couple to the acid by a covalent bond. Coupling to the acid may be through carbon, oxygen, silicon, sulfur, nitrogen and the like. Coupling through carbon or an oxygen-carbon group is presently preferred.

When, in the organophosphorus compound, n is 2, the end product occurs in the bis configuration. In this configuration, R must contain two or more carbon atoms, preferably from two to about 20 carbon atoms, such that at least two carbon atoms separate the phosphorus atoms. In such a configuration R can be considered to have a phosphate or phosphonate termination. In this bis configuration, no single carbon atom is bonded directly or indirectly to more than one $(PO(OH)_2)$ group. Thus, the groups which link to the metal have the basic structural formula:

wherein R'' is a bis group containing at least two carbon atoms bonded directly or indirectly to phosphorus and such that no phosphorus atoms are bonded directly or indirectly to the same carbon atom. The basic structures of the inorganic polymer forms are shown in FIGS. 14-16.

When coupling is through carbon, the organophosphorus acid compound is an organophosphoric acid and the product a phosphonate. When coupling is through oxygen-carbon, the organophosphorus acid compound is an organophosphoric monoester acid and the product a phosphate.

The general reaction for phosphonic acids alone is shown in equation (1) below and for monoesters of phosphoric alone by equation (2).

$$M^{+4} + 2(HO)_2OPR \longrightarrow M(O_3P-R)_2 + 4H^+ \quad (1)$$

$$M^{+4} + 2(HO)_2OP-OR' \longrightarrow M(O_3P-OR')_2 + 4H^+ \quad (2)$$

wherein R' is the remainder of the organo group.

The product contains phosphorus to metal in a molar ratio of about 2 to 1, and the empirical formula for the product would show all groups bound to phosphorus.

As used herein, R is an acyclic group, heteroacyclic group, alicyclic group, aromatic group or heterocyclic group.

The term "acyclic group," as used herein, means a substituted or unsubstituted acyclic group. The term "acyclic" includes saturated and unsaturated aliphatics which can be straight chain or branched chain. The "aliphatics" include alkyl, alkenyl and alkynyl.

The term "heteroacyclic group," as used herein, means an acyclic group containing one or more heteroatoms in the chain selected from oxygen, nitrogen and sulfur. The heteroatoms can be the same or different in each chain and usually the number of heteroatoms is one, two or three.

The term "alicyclic group," as used herein, means a substituted or unsubstituted alicyclic group. The term "alicyclic" includes saturated or unsaturated cyclic aliphatics.

The term "aromatic groups," as used herein, means a substituted or unsubstituted aromatic group. The term "aromatic" includes phenyl, naphthyl, biphenyl, anthracyl and phenanthryl.

The term "heterocyclic group," as used herein, means a subsituted or unsubstituted heterocyclic group. The term "heterocyclic" means an alicyclic or aromatic group containing one or more heteroatoms in the ring selected from oxygen, nitrogen and sulfur. The heteroatom can be the same or different in each ring and usually the number of heteroatoms is one, two or three.

The terms "substituted acyclic," "substituted heteroacyclic," "substituted alicyclic," "substituted aromatic" and "substituted heterocyclic," as used herein, mean an acyclic, heteroacylic, alicyclic, aromatic or heterocyclic group substituted with one or more of the groups selected from alkyl, alkenyl, alkynyl, alkoxy, alkenyloxy, alkynyloxy, alkylthio, alkenylthio, alkynylthio, halo, oxo, hydroxy, carbonyl, carboxy, alkylcarbonyloxy, alkylcarbonyl, carboxyalkyl, thio, mercapto, sulfinyl, sulfonyl, imino, amino, cyano, nitro, hydroxyamine, nitroso, cycloalkyl, cycloalkalkyl, aryl, aralkyl, alkaryl, aryloxy, arylalkoxy, alkaryloxy, arylthio, aralkylthio, alkarylthio, arylamino, aralkylamine and alkarylamino.

Figure 4:
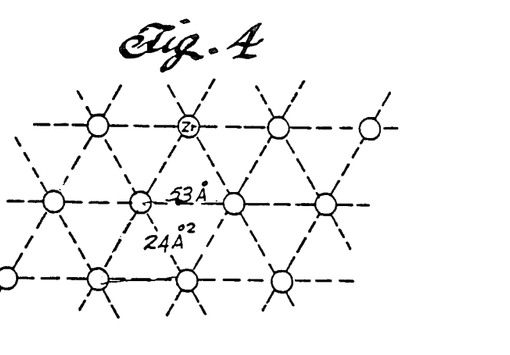
FIG. 4 illustrates a projection of a zirconium plane showing accepted spacing between Zr atoms and the available linkage area.
Figure 5:
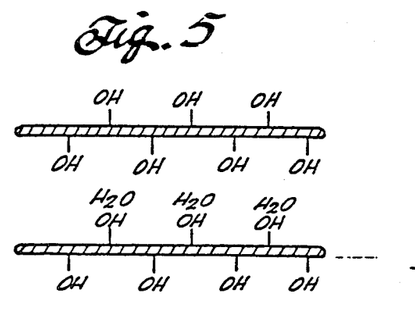
FIG. 5 is a symbolized depiction of spaced zirconium phosphate layers showing covalently bonded hydroxyl groups and water of hydration.

In general, with phosphorus as the pentavalent metal, the organo group should occupy no more than about 24 $\text{Å}^2$ for proper spacing. This limitation is imposed by the basic crystal structure of zirconium phosphate. Referring to FIG. 4, a spacing of 5.3 Å is shown between zirconium atoms in the zirconium plane of a crystal a total area of about 24 $\text{Å}^2$ is shown for the space bounded by zirconium atoms. It follows that any group anchored on each available site cannot have an area much larger than the site area and maintain the layered structure.

This limitation can be avoided through the use of a combination of larger and smaller groups, i.e., mixed components. If some of the sites are occupied by groups which have an area much less than about 24 $\text{Å}^2$, adjacent groups can be somewhat larger than 24 $\text{Å}^2$ and still maintain the layered structure of the compound.

The cross-sectional area which will be occupied by a given organo group can be estimated in advance of actual compound preparation by use of CPK space filling molecular models (Ealing Company) as follows: A model of the alkyl or aryl chain and terminal group is constructed, and it is situated on a scaled pattern of a hexagonal array with 5.3 Å site distances. The area of the group is the projection area on this plane. Some areas which have been determined by this procedure are listed in Table I.

TABLE I

| Moiety | Minimum Area ($\text{Å}^2$) | Moiety | Minimum Area ($\text{Å}^2$) |
|---|---|---|---|
| Alkyl chain | 15 | Isopropyl | 22.5 |
| Phenyl | 18 | t-butyl | 25 |
| Carboxyl | 15 | Chloromethyl | 14 |
| Sulfonate | 24 | Bromoethyl | 17 |
| Nitrile | 9 | Diphenylphosphine | 50 (approx.) |
| Morpholinomethyl | 21 | Mercaptoethyl | 13.5 |
| Trimethylamino | 25 | | |

The process for the formation of the novel inorganic polymers is a metathesis reaction conducted in the presence of a liquid medium receptive to the tetravalent metal ion at a temperature up to the boiling point of the liquid medium, preferably from ambient to about 150° C. and, more preferably, to about 100° C. at the pressure employed.

While water is the preferred liquid medium with phosphorus, as most of the organophosphorus acid compounds are hygroscopic, an organic solvent, such as ethanol can be employed, where water interferes with the reaction. There need only be provided a solvent for the organo-substituted pentavalent metal acid compound since the tetravalent ion can be dispersed as a solid in the solvent for slow release of the metal ion for reaction with the acid, e.g., the organophosphorus acid compound. If it has a sufficiently low melting point, the organo-substituted pentavalent metal acid compound can serve as a solvent. Typically, the liquid medium is the liquid medium in which the organo-substituted pentavalent metal acid is formed.

To illustrate with phosphorus acids, for complete consumption of the tetravalent compound, the amount of acid employed should be sufficient to provide two moles of phosphorus per mole of tetravalent metal. An excess is preferred. Phosphorous acid and/or phosphoric acid, if present, enters into the reaction and provides an inorganic polymer diluted in respect of the organo group in proportion to the amount of phosphorous or phosphoric acid employed.

Reaction is virtually instantaneous at all temperatures leading to precipitation of layered crystalline, semicrystalline or amorphous solid inorganic polymer.

The amorphous phase appears as a gel similar to silica gel. The gel can be crystallized by extended reflux in the reaction medium, usually from about 5 to about 15 hours. The semicrystalline product is characterized by a rather broad X-ray powder pattern (see FIGS. 7 and 8).

The presence of sequestering agents for the metal ion slows down the reaction and also leads to more highly crystalline products. For instance, a semicrystalline solid was prepared by the aqueous phase reaction of zirconium chloride and excess 2-carboxyethyl phosphonic acid, followed by 15 hours of reflux. A highly crystalline modification was prepared under identical conditions except that hydrogen fluoride was added to the reaction mixture. A slow purge of $N_2$ over the surface of the reaction solution slowly removed the fluoride from the system. Fluoride is a very strong complexing agent for zirconium ions. The slow removal of fluoride results in slow release of the metal ion for reaction The high surface area of the crystalline products also makes them useful for sorption of impurities from aqueous and nonaqueous media.

Another utility is as an additive to polymeric compositions. Similar to the high aspect ratio provided by solids such as mica which improve the stress strain properties of the polymers, the powdered inorganic polymer products of the invention can serve the same function and add features. By the presence of reactive end groups on the bonded organo groups, chemical grafting to the polymer network can be achieved to increase composite crystallinity and elevating heat distortion temperature. In addition, the presence of phosphorus induces flame retardant properties, as would bound halogen.

Still other utilities include solid lubricants which behave like mica, graphite and molybdenum disulfide; solid slow release agents were intercalated materials can be slowly leached or released from the internal layers of the crystals; substance displaying electrical, optical phase or field changes with or without doping, and the like.

While nowise limiting, the following examples are illustrative of the preparation of solid inorganic polymers of this invention and some of their utilities.

In the examples conducted in the atmosphere, no extraordinary precautions were taken concerning oxygen or moisture. Reagents were usually used as received from suppliers. The products formed are insoluble in normal solvents and do not sublime. However, the combined weight of yield data, spectroscopy, elemental analyses, TGA and powder diffraction results confirm the compositions reported with good reliability.

X-ray powder patterns were run on a Phillips diffractometer using CuK radiation.

Thermal analyses were conducted on a Mettler instrument. Infrared spectra were obtained with a Beckman Acculab spectrophotometer.

Surface areas were determined using both dynamic flow method, on a Quantasorb instrument, and also with a vacuum static system on a Micromeritic device. Both employ a standard BET interpretation of nitrogen coverage.

Titrations were carried out in aqueous or alcoholic medium. A standard combination electrode and an Orion Ionalyzer pH meter were used for pH determination. The titration of the solid interlamellar anchored materials is analogous to the titration of an ion exchange resin.

EXAMPLE 1

Figure 7:
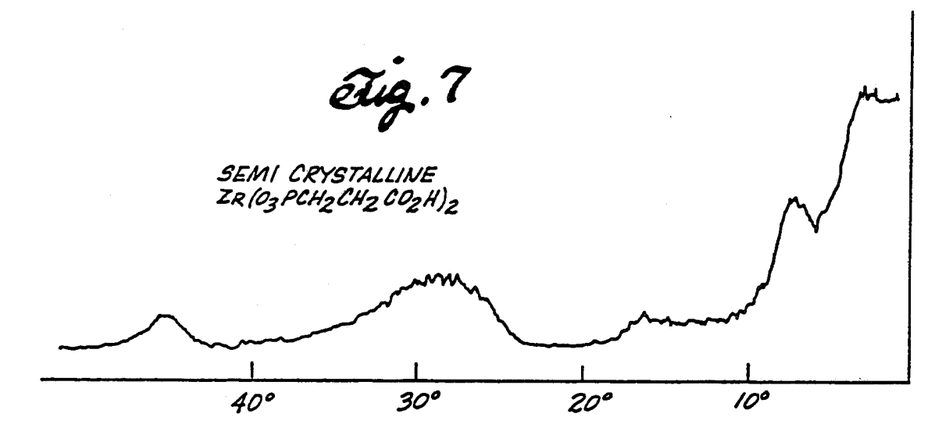
FIG. 7 is an X-ray powder diffraction pattern for semicrystalline zirconium 2-carboxyethyl phosphonate as prepared in Example 1.

To a 250 ml three-necked flask fitted with a reflux condenser, stirrer, thermometer and heating mantle, there was charged 21.8 ml of a 38% aqueous solution providing 11.1 g of 2-carboxyethylphosphonic acid in 25 ml of water. Stirring was commenced at room temperature and 9.2 g of $ZrOCl_2$ in 10 ml of water was added. A white precipitate was immediately formed. Water (17 ml) was added to fluidize the solids and temperature raised to about 90° to about 100° C. to gentle reflux which was continued for 15 hours. The slurry was cooled to room temperature and the white solid isolated by filtration. The solid was washed on the filter with water, acetone, then ether. The solid product was dried to a constant weight of 12.1 g determined to be semicrystalline and to have the empirical formula $Zr(O_3PCH_2CH_2COOH)_2$. The X-ray powder diffraction pattern is shown in FIG. 7.

EXAMPLE 2

The procedure of Example 1 repeated except that 4 ml of a 48% aqueous solution of hydrogen fluoride was added to the initial mixture and slowly removed by a slow purge of nitrogen maintained during reflux. The observed to calculated atomic composition was as follows:

| Atom | Observed | Calculated |
|------|----------|------------|
| C | 18.4% | 18.23% |
| H | 2.84% | 2.54% |
| P | 15.5% | 15.7% |

Figure 8:
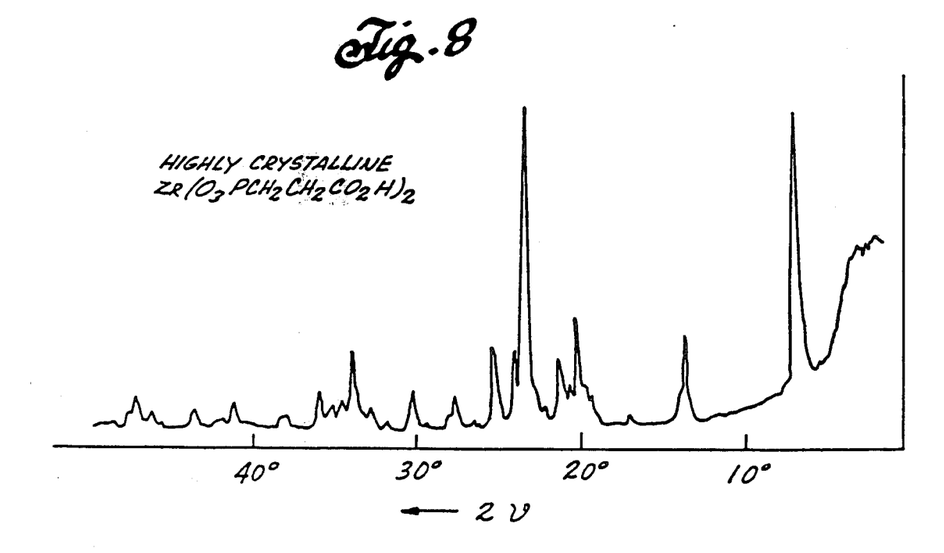
FIG. 8 is an X-ray powder diffraction pattern for highly crystalline zirconium 2-carboxyethyl phosphonate as prepared in Example 2.
Figure 9:
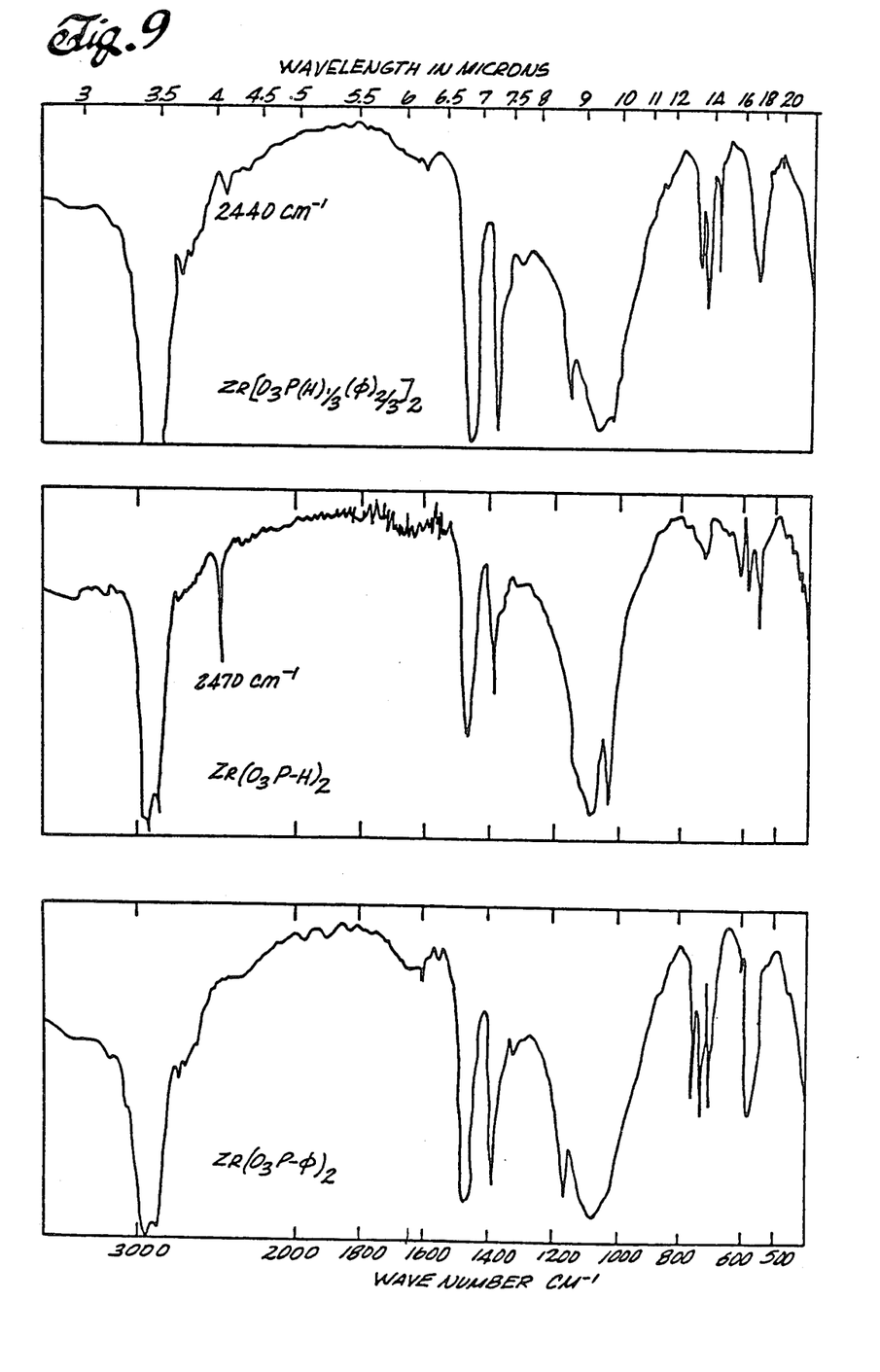
FIG. 9 is infrared spectra for a mixed component product $Zr(O_3P(H)_{1/3},\phi_{2/3})_2$ as compared to the pure phases $Zr(O_3P\phi)_2$ and $Zr(O_3PH)_2$ where $\phi$ is the radical $-C_6H_5$.

The X-ray diffraction pattern for the highly crystalline product is shown in FIG. 8. Interlayer spacing was determined to be 12.8 Å.

EXAMPLES 3-51

Using the method detailed in Example 1 or Example 2, the following compounds were prepared from the reagents listed. The inorganic polymer compounds produced, reagents used, elemental analysis of product, interlayer spacing and polymer structure are listed in the following Table III. In the examples set forth in Table III the $M^{+4}$ salt used was $ZrOCl_2.8H_2O$ with the exception that for examples 15 and 27 the salt was $Zr(OC_3H_7)_4$. In the last column on the right designated "Str.," the letters C, S and A are used to refer to structures of the compounds that are crystalline, semicrystalline and amorphous respectively. The interlayer spacings for the compounds were determined using X-ray powder diffraction techniques. In the column designated "Other" the elements analyzed are listed immediately following the weight percentage determined.

TABLE III

| Ex. | Compound Produced | Product Wt.g | Phosphorus or Arsenic Reagent Used | Acid Wt.g | $M^{+4}$ Salt Wt.g | Weight Percent C | H | other | Interlayer Spacing Å | Str. |
|-----|-------------------|--------------|-----------------------------------|-----------|--------------------|------|------|-------|---------------------|------|
| 3 | $Zr(O_3PCH_2Cl)_2$ | 5.898 | $H_2O_3PCH_2Cl$ | 46 | 5.50 | 6.53 | 1.26 | 17.38Cl | 10.0 | C |
| 4 | $Zr(O_3PCH_2CH_2N^+H_3{}^-Cl)_2$ | 0.824 | $H_2O_3PCH_2CH_2N^+H_3{}^-Cl$ | 0.504 | 0.638 | 11.98 | 4.67 | 6.450 | 14.3 | S |
| 5 | $Zr(O_3P(CH_2)_3PO_3)$ | 1.05 | $H_2O_3P(CH_2)_3PO_3H_2$ | 0.787 | 0.681 | 12.70 | 3.58 | 20.7 P | | A |
| 6 | $Zr(O_3PCH_3)_2$ | 0.867 | $H_2O_3PCH_3$ | 0.814 | 0.751 | 8.84 | 2.95 | | | A |
| 7 | $Zr(O_3PCH_2C_6H_5)_2$ | 2.280 | $H_2O_3PCH_2C_6H_5$ | 2.002 | 1.035 | 30.01 | 3.96 | | 14.7 | S |
| 8 | $Zr(O_3PCH_2CH=CH_2)_2$ | 5.703 | $(EtO)_2OPCH_2CH=CH_2$ | 9.90 | 3.69 | 20.5 | 3.56 | | | A |
| 9 | $Zr(O_3PCH_2CH_2{}^+N\diagup\diagdown{}^-Br)_2$ | 4.61 | $(EtO)_2OPCH_2CH_2Br$ | 5.00 | 1.736 | | | | | A |
| 10 | $Zr(O_3P(CH_2)_{10}PO_3)$ | 1.27 | $(EtO)_2OPC_{10}H_{20}PO(OEt)_2$ | 15.05 | 0.64 | 31.22 | 6.11 | | 17.3 | S-A | with the phosphonic acid, resulting in an increase in crystallinity.

A similar enhancement of crystallinity was obtained in the reaction of thorium nitrate with 2-carboxyethyl phosphonic acid. Nitrate ion is a sequestering agent for thorium and the rate of formation of this product is slow and the product polymer quite crystalline.

As compared to zirconium phosphate forming crystals of 1–5 microns, crystals of 100 to greater than 1000 microns in size have been prepared in accordance with the invention.

A critical property for many of the likely uses of the products is their thermal stability. This is because deficiencies in activity can be compensated for by reasonable increases in operating temperature. A standard method for thermal characterization is thermal gravimetric/differential thermal analysis (TGA/DTA). These techniques indicate changes in weight and heat flow of substances as a function of temperature. Thus, decomposition and phase changes can be monitored as temperature increases.

Zirconium phosphate itself is quite a stable material. Interlayer water is lost at about 100° C., and a second dehydration involving the phosphates occurs above 400° C. The practical ion-exchanging abilities are lost in this step.

The inorganic phosphorus-containing polymers of this invention are also stabilized toward thermal decomposition as compared to pure inorganic analogs as a result of the fixation and separating effect of the inorganic support.

For zirconium chloromethyl phosphonate, for instance, weight loss did not commence until well above 400° C. The organic fragment was half lost at about 525° C., indicating remarkable stability. Decomposition of zirconium 2-carboxyethylphosphonate begins between 300° and 400° C. The decomposition process inflection point, approximate midpoint, falls at about 400° C.

While not bound by theory, phosphates probably decompose like carboxylic esters to yield acid and unsaturates, whereas phosphonates likely form radicals by homolytic cleavage. Both nitrophenyl and cyanoethyl phosphates of zirconium decompose at about 300° C. The phenylphosphonate decomposes at about 425° C.

Besides proving the suitability of such compounds in elevated temperature applications, the TGA analysis affirmed covalent bonding to phosphorus. This is because normal intercalative interactions are reversed within 10° to 100° C. above the boiling point of the guest.

The process of this invention permits a wide variety of inorganic polymers to be formed having the characteristic of the organo group protected by the inorganic polymer structure and with subsequent exchange or substitution reactions, the formation of other inorganic polymers. Polymers formed may be block, random and the like.

For instance, a mixture of phenyl phosphonic acid and phosphorous acid was simultaneously reacted with zirconium ion to yield a single solid phase. The interlamellar distance was the same as zirconium phenyl phosphonate, or about 15.7 Å. There was no reflection at 5.6 Å, the normal spacing for zirconium phosphite. This established that the largest group should determine interlamellar distance and indicated that a discreet zirconium phosphate phase was not present. Evidence of a change in chemical environment of P-H band was established by infrared analysis. In infrared analysis of zirconium phosphite, P-H stretching is observed as a sharp band at 2470 cm$^{-1}$ (moderate intensity). In the mixed compound solid, this band was shifted to 2440 cm$^{-1}$ and broadened.

Figure 6:
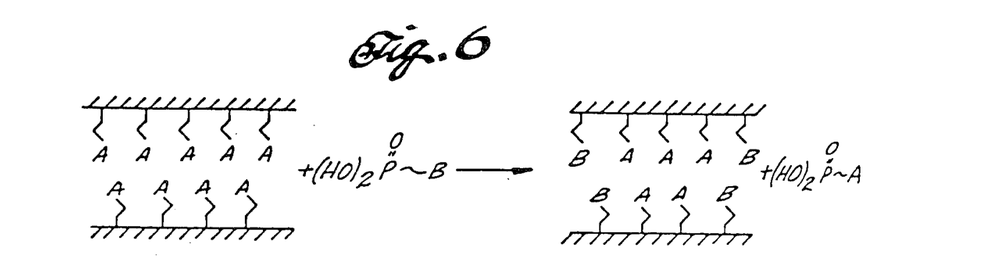
FIG. 6 illustrates an exchange reaction between anchored groups "A" and groups to be substituted for "B," and represents the portion of the organo group linking the terminal group "A" or "B" to the crystals or the organophosphorus acid compound reactant.

Another route is to exchange one pendant group for another. The exchange reaction is described in Example 131. While not bound by theory, the present expected points of exchange are at the periphery of the crystal and are schematically illustrated in FIG. 6. Such bifunctional materials exhibit the quality of providing terminal groups for attracting species for intercalation and then interaction with the internal groups.

The reaction of bis acids with tetravalent metal ions permits interlamellar cross-linking by a reaction such as whereas in FIG. 6, represents the interlamellar layers to which the alkyl group is anchored. As with all organo groups, for the bis configuration at least two carbon atoms are present, preferably from two to twenty atoms, and the phosphorus atoms are linked directly to indirectly to different carbon atoms. Since size of the linking group will control and fix interlamellar spacing, there is provided effective laminar sieves of fixed spacing for application analogous to that of molecular sieves.

Ion exchange activity was established with pendant carboxylic acid groups. Prepared zirconium 2-carboxyethyl phosphonate was established to have an interlayer distance of 12.8 Å. When intercalated to form its n-hexylammonium salt, the interlayer distance increased to 27.2 Å. When sodium was taken up, layer spacing increased to 14.2 Å. X-ray and infrared data indicated the highly crystalline inorganic polymer to behave as expected for a carboxylic acid, with behavior analogous to ion exchange resins, except that both external and internal surfaces were functional, establishing them as super surface ion exchange resins. Moreover, since the inorganic polymers can be prepared as microcrystalline powders, diffusion distances are short.

As summarized in Table II, nitrile and mercapto anchored groups show the ability to take up silver and copper ions at room temperature for catalytic activity.

TABLE II

| Anchored Group | Metal Ion | Loading MMole Metal MMole Zr |
| --- | --- | --- |
| —O~CN | 0.1 M Ag+ | 0.20 |
| ~SH | 0.1 M Ag+ | 1.0 |
| —O~CN | 0.1 M Cu++ | 0.10 |
| —O~CN | 0.1 M Cu++ 0.5 M HOAc 0.5 M NaAc | 0.10 |

~ = groups formed of carbon and hydrogen.
Ac = acetate radical

The alternate to catalytic utility is to attach the metals to the organophosphorus acid prior to reaction with the soluble tetravalent metal compound.

TABLE IV-continued

| Compound Produced | Product Wt.g | Phosphorus Reagent Used | Acid Wt.g | M+4Salt | Salt Wt.g | Weight Percent C | H | Other | M+4 | Interlayer Spacing Å | Structure |
|---|---|---|---|---|---|---|---|---|---|---|---|
| Th(O$_3$PCH$_2$OH)$_2$ | 1.13 | H$_2$O$_3$PCH$_2$OH | 0.552 | Th(NO$_3$)$_4$ | 1.35 | 2.30 | 2.26 | | | 9.51 | C |
| Th(O$_3$PC$_{18}$H$_{37}$)$_2$ | 1.1 | (CH$_3$O)$_2$OPC$_{18}$H$_{37}$ | 0.952 | Th(NO$_3$)$_4$ | 0.726 | 46.57 | 8.43 | | 20.9 | 42 | C |
| Ti(O$_3$PCH=CH$_2$)$_2$ | 7.1 | Na$_2$O$_3$PCH=CH$_2$ | 9.44 | TiCl$_4$ | 16.3 | | | | | | |
| Th(O$_3$PCH=CH$_2$)$_2$ | 7.9 | Na$_2$O$_3$PCH=CH$_2$ | 10.6 | Th(NO$_3$)$_4$ | 21.0 | | | | | | |
| Th(O$_3$PCH$_2$CH$_2$COOH)$_2$ | | | | | | | | | | | |
| Ti(O$_3$PCH$_3$)$_2$ | 0.919 | H$_2$O$_3$PCH$_3$ | 0.913 | TiOCl$_2$ | 0.640 | 6.54 | 4.54 | 17.5 P | | | Amorphous |
| Th(O$_3$PCH$_3$)$_2$ | 1.704 | H$_2$O$_3$PCH$_3$ | 0.845 | Th(NO$_3$)$_4$ | 2.252 | 4.78 | 2.21 | | 51.4 | 8.92 | |

EXAMPLES 65–86

Using the method outlines in Example 1, the following compounds are prepared:

| Ex. | | |
|---|---|---|
| 65 | M(O$_3$P—(CH$_2$)$_n$—PR$_2$)$_2$ | M = Ti$^{+4}$, Zr$^{+4}$, Hf$^{+4}$, U$^{+4}$, Th$^{+4}$, Ce$^{+4}$, Pb$^{+4}$, n = 1–10, R = =CH$_3$, —C$_2$H$_5$, —C$_6$H$_5$. |
| 66 | M(O$_3$P—(CH$_2$)$_n$—CH$_3$)$_2$ | M as above and n = 1–22. |
| 67 | M(O$_3$P—(CH$_2$)$_n$—OP(OR)$_2$)$_2$ | M, n, R as above. |
| 68 | M(O$_3$P—(CH$_2$)$_n$—$\overset{+}{N}$(CH$_3$)$_3$X$^-$)$_2$ | M, n as above; X = halide, sulfate nitrate, phosphate, acetate. |
| 69 | M(O$_3$P—CH$_2$—C$_6$H$_4$X)$_2$ | M and X as above. |
| 70 | M(O$_3$P—(CH$_2$)$_n$—NH—CS$_2$H)$_2$ | M, n as above. |
| 71 | M(O$_3$P(CH$_2$)$_n$—N(CH$_2$CO$_2$H)$_2$ | M, n as above. |
| 72 | M(O$_3$P(CH$_2$)$_n$—$\overset{+}{N}$H$_2$—(CH$_2$)$_3$SO$_3$$^-$)$_2$ | M, n as above. |
| 73 | M(O$_3$P—(CH$_2$)$_n$—NC)$_2$ | M, n as above. |
| 74 | M(O$_3$P—(CH$_2$)$_n$—C≡CH)$_2$ | M, n as above. |
| 75 | M(O$_3$P—(CH$_2$)$_n$—C$_6$H$_4$-C$_6$H$_3$(-N)(-N))$_2$ | M, n as above. |
| 76 | M(O$_3$P—(CH$_2$)$_n$—SR)$_2$ | M, n as above; R = —CH$_3$, —C$_2$H$_5$ |
| 77 | (M(O$_3$P—(CH$_2$)$_n$—C$_5$H$_4$)$_2$ | M, n as above. |
| 78 | (M(O$_3$P—(CH$_2$)$_n$CH=O)$_2$ | M, n as above. |
| 79 | M(O$_3$P—(CH$_2$)$_n$—C$_6$H$_4$Cl)$_2$ | M, n as above. |
| 80 | M(O$_3$P—(CH$_2$)$_n$—C$_6$H$_4$-Fe-C$_6$H$_4$)$_2$ | M, n as above. |
| 81 | M(O$_3$P—(CH$_2$)$_n$—C(SH)=CH(SH))$_2$ | M, n as above. |
| 82 | M(O$_3$P—(CH$_2$)$_n$-C$_6$H$_4$R)$_2$ | M, n as above, R = —CH$_3$, —C$_2$H$_5$, —CH(CH$_3$)$_2$ or —C(CH$_3$)$_3$ as in 1. |
| 83 | M(O$_3$P—(CH$_2$)$_n$OPR$_2$)$_2$ | M, n and R as in 1. |
| 84 | M(O$_3$P—(CH$_2$)$_n$—Br$_2$)$_2$ | M, n and R as in 1, or R = H. |
| 85 | M(O$_3$P—(CF$_2$)$_n$—SO$_3$H)$_2$ | M, n as above. |
| 86 | Compounds above in which the P—(CH$_2$)$_n$ linkage is replaced by a P—O—(CH$_2$)$_n$ link. | |

EXAMPLE 87

The usefulness of the zirconium 2-carboxyethyl phosphonate formed in Example 28 was shown in an experiment which tested the ability of the compound to extract copper ions from aqueous solutions.

In the experiment, 1.00 g of the zirconium 2-carboxyethyl phosphonate was mixed with 40 ml of 0.103 M copper solution having a pH of 4.01 and, after about 30 minutes, a 10 ml aliquot of the solution phase was removed, its pH being 2.19. The remaining slurry was treated with 4 ml of 2.5 percent of sodium hydroxide solution and, after about 10 minutes, the liquid, with a pH of 3.93, was removed. A second 1.11 g portion of the zirconium 2-carboxyethyl phosphonate was mixed with 40 ml of the 0.103 M copper solution, and 2.0 ml of 2.5 percent sodium hydroxide solution was added. After about 15 minutes, a 10 ml aliquot of the supernatant liquid, which has a pH of 3.39, was removed. The remaining slurry was treated with 5.0 ml of 2.5 percent sodium hydroxide solution and after about 30 minutes, the supernatant liquid having a pH of 4.85 was removed.

TABLE III-continued

| Ex. | Compound Produced | Product Wt.g | Phosphorus or Arsenic Reagent Used | Acid Wt.g | $M^{+4}$ Salt Wt.g | Weight Percent C | II | other | Interlayer Spacing Å | Str. |
|---|---|---|---|---|---|---|---|---|---|---|
| 11 | $Zr(O_3PCH_2CH_2PO_3)$ | 5.16 | $(EtO)_2OPCH_2CH_2PO(OEt)_2$ | 22 | 5.6 | | | | | |
| 12 | $Zr(O_3PCH_2CH_2Cl)_2$ | 134.96 | $H_2O_3PCH_2CH_2Cl$ | 78.25 | 94.64 | | | | | |
| 13 | $Zr(O_3PCH_2CH_2Br)_2$ | 8.6 | $(EtO)_2OPCH_2CH_2Br$ | 24.5 | 6.2 | | | | 13 | |
| 14 | $Zr(O_3PCH_2CH_2CN)_2$ | 6.45 | $(EtO)_2OPCH_2CH_2CN$ | 6.365 | 6.035 | 18.72 | 2.28 | 7.30N | 11.79 | C |
| 15 | $Zr(O_3PCH_2{-}N{-})_2$ | 0.166 | $(C_8H_7O)OPCH_2{-}N{-}$ | | 2.30 | | | | | |
| 16 | $Zr(O_3PCH_2CH_2CO_2H)_2$ | 12.1 | $(EtO)_2OPCH_2CH_2CO_2CH_2CH_3$ | 00 | 9.20 | 10.63 | 3.45 | 13.1 P | | C |
| 17 | $Zr(O_3PCH_2CH_2SO_3H)_2$ | 4.3 | $(EtO)_2OPCH_2CH_2SO_2$ | 7.7 | 3.3 | | | | 17.3 | C |
| 18 | $Zr(O_3P(CH_2)_{10}PO_3)_{4/3}(O_3POH)_{\frac{2}{3}}$ | 5.9 | $(EtO)_2OPC_{10}H_{20}PO(OCH_2CH_3)_2$ | 15.05 | 1.92 | | | | | |
| 19 | $Zr(O_3PCH_2CH_2CN)_2$ | 2.886 | $BaO_3PCH_2CH_2CN$ | 6.311 | 2.199 | 17.12 | 2.89 | | | S |
| 20 | $Zr(O_3PH)_{\frac{2}{3}}(O_3PCH_2CH{=}CH_2)_{4/3}$ | 2.645 | $(EtO)_2OPCH{=}CH_2$ | 9.90 | 1.846 | 15.40 | 3.13 | | | A |
| 21 | $Zr(O_3P(CH_2)_{10}PO_3)_{\frac{1}{3}}(O_3POH)_{\frac{2}{3}}$ | 3.28 | $(EtO)_2OPC_{10}H_{20}PO(OEt)_2$ | 15.05 | 1.92 | 13.95 | 4.06 | | 17.3 | S |
| 22 | $Zr(O_3POCH_2CH_2CN)_{\frac{2}{3}}(O_3POH)_{4/3}$ | 1.984 | $BaO_3POCH_2CH_2CN$ | 3.27 | 1.353 | | | | | |
| 23 | $Zr(O_3PCH_2CH_2P\phi_2)_{\frac{2}{3}}(O_3PCH_3)_{4/3}$ | 1.230 | $H_2O_3PCH_2CH_2P\phi_2$ | 0.689 | 0.405 | | | | | |
| 24 | $Zr(O_3P(CH_2)_3P\phi_2)_{.4}(O_3PCH_3)_{1.6}$ | 3.605 | $H_2O_3(CH_2)_3P\phi_2$ | 2.31 | 1.603 | | | | | |
| 25 | $Zr(O_3PCH_2Cl)_{4/3}(O_3POH)_{\frac{2}{3}}$ | 6.75 | $H_2O_3PCH_2Cl$ | | 4.5 | | | | | |
| 26 | $Zr(O_3PCH_2\overset{+}{H}N{-}O\ Cl^-)_2$ | 6.5 | $H_2O_3PCH_2N{-}O$ | 5.64 | 5.01 | | | 16 | | |
| 27 | $Zr(O_3PCH_2OCH_2COCH_2CH_3)_2$ | 1.343 | $(EtO)_2OPCH_2OCH_2COEt$ | | 1.164 | | | | | |
| 28 | $Zr(O_3PCH_2CH_2CO_2H)_2$ | 12.1 | $(EtO)_2OPCH_2CH_2CO_2CH_2CH_3$ | 80 | 9.20 | 18.4 | 2.84 | 15.5P | 12.8 | C |
| 29 | $Zr(O_3PCH_2SH)_2$ | 7.3 | $H_2O_3PCH_2SH$ | 10 | 6.3 | 7.43 | 2.65 | 12.37S | | A |
| 30 | $Zr(O_3PCH_2CH_2SH)_2$ | 1.72 | $H_2O_3CH_2CH_2SH$ | 2.0 | 1.0 | 17.63 | 3.70 | 13.425 | 15.5 | C |
| 31 | $Zr(O_3PCH_2CH_2NH_2)_2$ | 0.82 | $H_2O_3PCH_2CH_2NH_2$ | 0.50 | 0.64 | | | | | |
| 32 | $Zr(O_3PCH_2CO_2H)_2$ | 15.3 | $H_2O_3PCH_2CO_2H$ | 16.1 | 13.5 | | | | 11.1 | C |
| 33 | $Zr(O_3PCH_2CH_2SO_3H)_2$ | 6.1 | $H_2O_3PCH_2CH_2SO_3H$ | 7.4 | 5.0 | | | | | A |
| 34 | $Zr(O_3PCH{=}CH_2)_2$ | 3.7 | $H_2O_3PCH{=}CH_2$ | 13.3 | 5.6 | | | | 6.92 | C |
| 35 | $Zr(O_3PCH_2OC_6H_5)_2$ | 4.3 | $H_2O_3PCH_2OC_6H_5$ | 4.9 | 3.7 | | | | 18 | C |
| 36 | $Zr(O_3PCH_2CH_2CH(\overset{O}{\overset{\|}{C}}{-}CH_3)_2)_2$ | 1.87 | $H_2O_3PCH_2CH_2CH(\overset{O}{\overset{\|}{C}}{-}CH_3)_2$ | 2.0 | 0.93 | | | | 11.3 | C |
| 37 | $Zr(O_3POCH_2CH_2CN)_2$ | 1.35 | $H_2O_3POCH_2CN$ | 6.3 | 1.1 | | | | 13.2 | |
| 38 | $Zr(O_3PCH_2CN)_2$ | 4.6 | $H_2O_3PCH_2CN$ | 4.6 | 4.3 | 14.60 | 2.13 | 3.49N | 10.8 | C |
| 39 | $Zr(O_3PCH_2CH_2CH_2SO_3H)_2$ | 10.1 | $H_2O_3PCH_2CH_2CH_2SO_3H$ | 14 | 9 | | | | 18.8 | |
| 40 | $Zr(O_3PCH_2CH_2CH_2PO_3H_2)$ | 0.45 | $H_2O_3PCH_2CH_2CH_2PO_3H_2$ | 0.79 | 0.34 | | | | | |
| 41 | $Zr(O_3P(CH_2)_3CO_2H)_2$ | 56.7 | $H_2O_3P(CH_2)_3CO_2H$ | 51.9 | 49.7 | | | | 14.8 | |
| 42 | $Zr(O_3PCH{=}CH_2)_2$ | 11.6 | $Na_2O_3PCH{=}CH_2$ | 12.0 | 23.9 | | | | | |
| 43 | $Zr(O_3P(CH_2)_4CO_2H)_2$ | | $H_2O_3P(CH_2)_4CO_2H$ | | | | | | 16.4 | |
| 44 | $Zr(O_3PCH_2CH_2CN)_2$ | 1.393 | $BaO_3PCH_2CH_2CN$ | 6.277 | 1.10 | 17.6 | 2.76 | 6.22N | 13.2 | C |
| 45 | $Zr(O_3PCH_2CH_2CN)_2$ | 2.886 | $BaO_3PCH_2CH_2CN$ | 6.311 | 2.199 | 17.12 | 2.89 | | | S |
| 46 | $Zr(O_3PCH_2CN)_2$ | 3.839 | $(EtO)_2OPCH_2CN$ | 4.045 | 2.034 | 16.53 | 2.76 | 5.54N | | A |
| 47 | $Zr(O_3PCH_2CH_2CH_2CN)_2$ | 1.8 | $(EtO)_2OPCH_2CH_2CH_2CN$ | 4.0 | 4.8 | | | | | |
| 48 | $Zr(O_3PCH_2SCH_2CH_3)_2$ | 2.146 | $(EtO)_2OPCH_2SCH_2CH_3$ | 4.00 | 1.66 | 17.30 | 3.89 | 15.3 S | 14.7 | |
| 49 | $Zr(O_3PCH_2CH_2CH_2SO_3H)_2$ | 4.3 | $(EtO)_2OPCH_2CH_2CH_2SO_3H$ | 7.7 | 3.3 | | | | 17.3 | C |
| 50 | $Zr(O_3PCH_2CH_2SO_3H)_2$ | 2.45 | $(EtO)_2OPCH_2CH_2SO_3H$ | | 7.4 | | | | | S |
| 51 | $Zr(O_2PCH_2CH_2\phi SO_3H)_2$ | 0.58 | $H_2O_3PCH_2CH_2\phi SO_3H$ | | 0.28 | | | | | |

EXAMPLES 52-64

Using the method outlined in Example 1 or Example 2, the inorganic polymers listed in the following Table IV were prepared. In Table IV the compound produced, phosphorus-containing reagent, $M^{+4}$ salt, elemental analysis of product, interlayer spacing and product structure are listed. The weights are listed in grams. When the $M^{+4}$ salt is listed as $Th(NO_3)_4$ it is meant $Th(NO_3)_4 \cdot 4H_2O$ was used in the example. In the column designated "Other" the element analyzed is listed following its determined weight percentage. The interlayer spacings for the compounds were determined using X-ray powder diffraction techniques. In the column designated structure the letters C, S and A are used to designate crystalline, semicrystalline and amorphous configurations respectively.

TABLE IV

| Compound Produced | Product Wt.g | Phosphorus Reagent Used | Acid Wt.g | $M^{+4}$ Salt | Salt Wt.g | Weight Percent C | II | Other | $M^{+4}$ | Interlayer Spacing Å | Structure |
|---|---|---|---|---|---|---|---|---|---|---|---|
| $U(O_3POCH_2CH_2CH)_2$ | 5.02 | $BaO_3POCH_2CH_2CN$ | 5.8 | $UCl_4$ | 3.8 | 11.67 | 2.12 | | | 13.8 | S to C |
| $Th(O_3PCH_2Cl)_2$ | 6.0 | $H_2O_3PCH_2Cl$ | 10.0 | $Th(NO_3)$ | 6.6 | 4.62 | 1.46 | 12.65 Cl | | 10.5 | C |
| $Ph(O_3PCH_2Cl)_2$ | 5.1 | $H_2O_3PCH_2Cl$ | 12.2 | $PbO_2$ | 3.9 | 3.65 | 7.2 | | | 9.83 | C |
| $U(O_3PCH_2Cl)_2$ | 0.4 | $H_2O_3PCH_2Cl$ | 0.55 | $UCl_4$ | 0.34 | | | | | 10.0 | C |
| $Ti(O_3PCH_2Cl)_2$ | 5.9 | $H_2O_3PCH_2Cl$ | 4.74 | $TiCl_4$ | 4.4 | 6.37 | 2.79 | 16.36 Cl | | 10.4 | C |
| $Th(O_3PCH_3)_2$ | 1.7 | $H_2O_3PCH_3$ | 0.845 | $Th(NO_3)_4$ | 2.25 | | | | | | | lyst. The slurry was refluxed and water removed azeotropically. After about one day, 40 ml of fresh butanol was added and azeotropic distillation continued for about a week. The product was isolated by filtration and washed with acetone and ethyl ether. The dry product weighed 5.44 g. The infrared spectrum clearly shows the conversion from the carboxylic acid to the ester. This material can be used as a host or carrier for biologically active organic molecules (e.g., methoprene).

EXAMPLE 96

The product of Example 49 was used as a catalyst in an esterification reaction. A 0.503 g portion was added to a distillation flask containing 2.85 ml of acetic acid and 2.85 ml of denatured ethanol. The mixture was heated and a distillate product collected. This product was identified by gas chromatography and infrared spectrophotometry as ethyl acetate.

The solid phase of the reaction mixture was recovered and weighed 0.51 g. Its X-ray diffraction pattern matched that of the initial material added.

EXAMPLE 97

A slurry of 0.100 g of the product from Example 49 and 1.0 g cyclohexanol was heated to 125° C. in a micro distillation apparatus. An essentially quantitative yield of cyclohexane was recovered in the distillate receiver, indicating utility of the zirconium 3-sulfopropylphosphonate as a catalyst for dehydrating alcohols.

EXAMPLE 98

Diethyl 2-carboethoxyethyl phosphonate was prepared by the Arbuzov reaction of triethyl phosphite and ethyl 3-bromopropionate. The phosphonate ester product was hydrolyzed to the acid in refluxing HBr and then reacted in situ with zirconium ion. The resultant layered compound, zirconium 2-carboxyethyl phosphonate, had interlamellar carboxylic acid substituents. The highly crystalline modification had an interlayer distance of 1.28 Å and its n-hexylammonium salt was determined to have an interlayer spacing of 27.6 Å. The thorium salt of 2-carboxyethyl phosphonate was also prepared in an analogous manner.

The interlamellar carboxylic acid was determined to have a strong carbonyl stretching frequency at 1710 $cm^{-1}$. Upon sodium salt formation, this shifts to 1575 and 1465 $cm^{-1}$. The X-ray powder pattern of the sodium salt indicates a layer spacing of 14.2 Å. The X-ray and infrared data of the interlamellar carboxylic acid and its salts indicate that this material behaves as a carboxylic acid. This IR behavior is analogous to that of ion exchange resins with carboxylic functionality.

Figure 10:
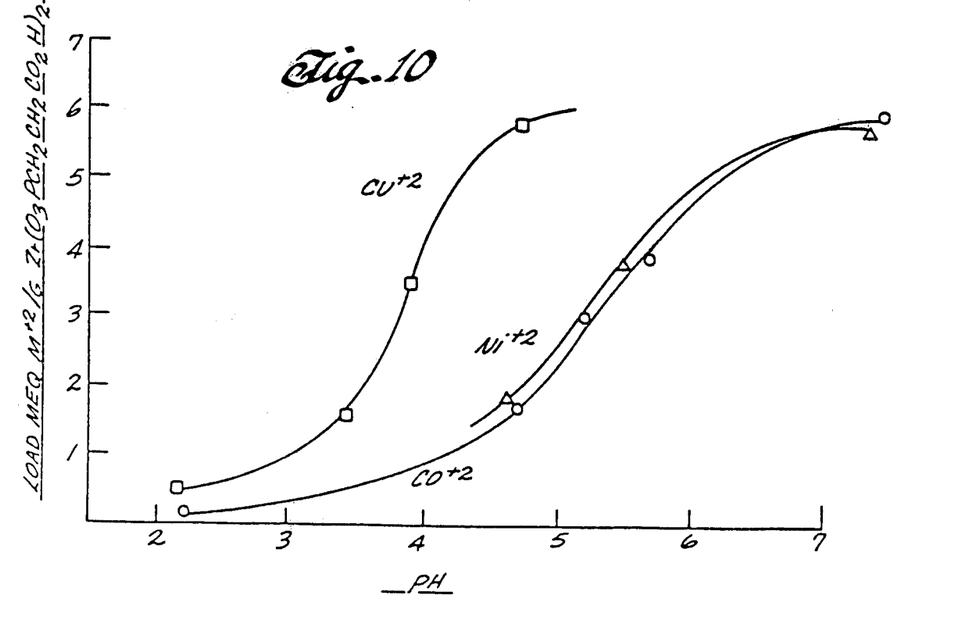
FIG. 10 compares the loading of divalent metals on zirconium 2-carboxyethyl phosphonate as a function of pH.

The ion exchange behavior of the interlamellar carboxylic acid was investigated with a number of metals. FIG. 10 represents the pH versus loading profile for the $2H^+$-$M^{+2}$ exchange of $Cu^{+2}$, $Ni^{+2}$, and $Co^{+2}$ with semicrystalline zirconium 2-carboxyethyl phosphonate. These profiles are in the normal pH rnge for the exchange of these metals with carboxylic acids.

Figure 11:
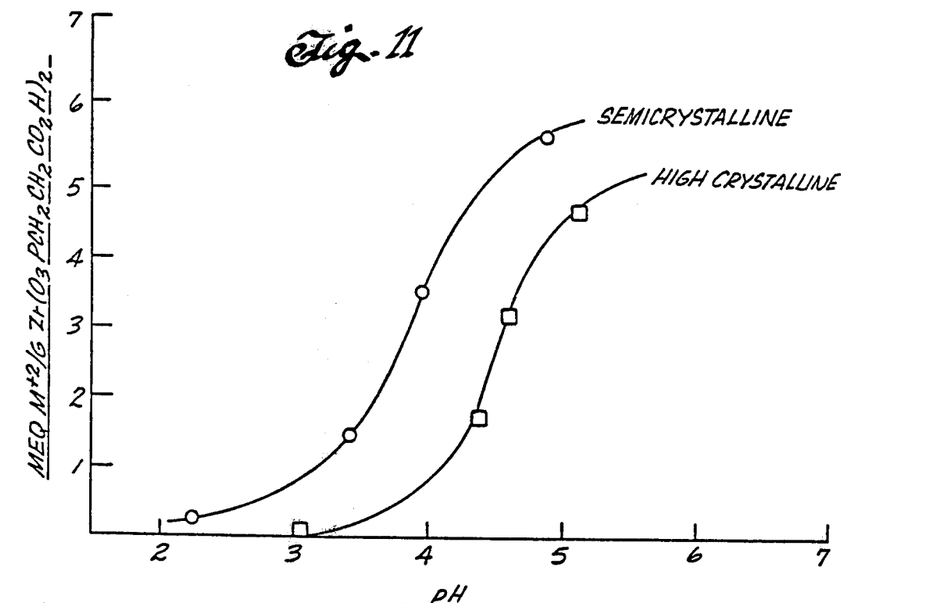
FIG. 11 compares the loading of $Cu^{+2}$ in the semicrystalline reaction product of Example 1 (Example 28) to the highly crystalline product of Example 2.

The influence of crystallinity of the $H^+$-$Cu^{+2}$ exchange equilibrium is demonstrated in FIG. 11. The $pH_{0.5}$ is about 3.8 for the semicrystalline and about 4.5 for the high crystalline. This indicates that the matrix supporting the anchored functional group influences the reactivity of the functional group.

Figure 12:
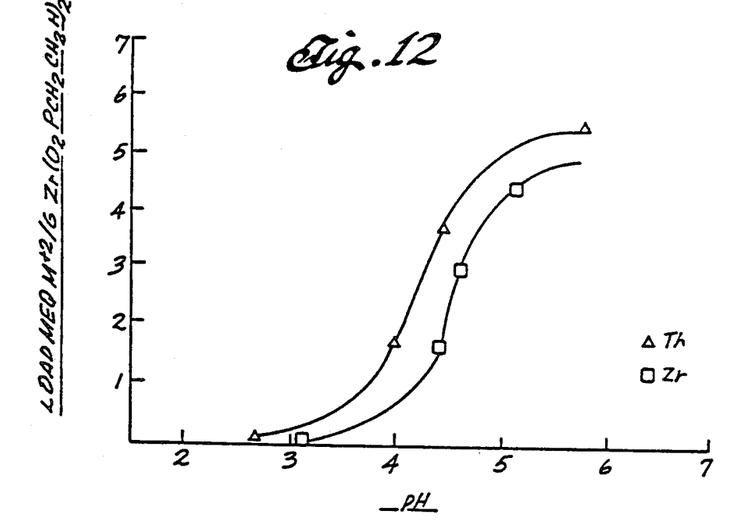
FIG. 12 compares the loading of $Cu^{+2}$ on the reaction product of Example 2 to thorium 2-carboxyethyl phosphonate.

The interlamellar metal ion also has an influence on the $H^+/Cu^{+2}$ exchange equilibrium. High crystallinity modifications of thorium and zirconium 2-carboxyethylphosphonate were compared. This data is presented in FIG. 12. The thorium compound is the stronger acid by about 0.3 pKa units in this reaction ($pH_{0.5}=4.2$ v 4.5).

EXAMPLE 99

Figure 13:
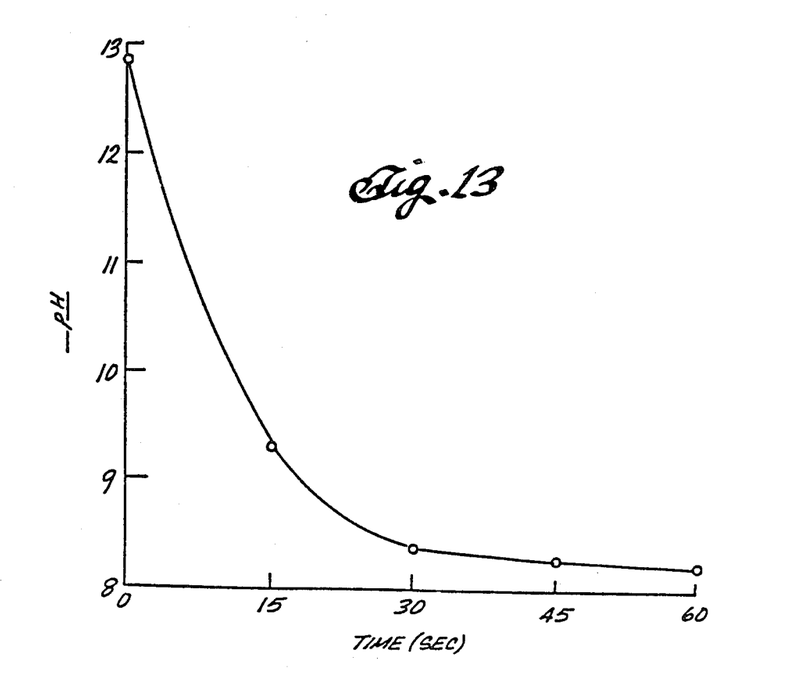
FIG. 13 shows the rate of neutralization of zirconium 2-carboxyethyl phosphonate by sodium hydroxide.

The reaction rate of zirconium 2-carboxyethyl phosphonate with aqueous sodium hydroxide was determined by its addition to an aqueous solution of NaOH with decrease in pH measured as a function of time. As shown in FIG. 13, the concentration of hydroxide ion changed by over three orders of magnitude in 15 seconds representing reaction of 80% of the carboxylic groups. This established that the interlamellar reaction was quite facile and diffusion into the crystal did not involve a high kinetic barrier. Prolonged exposure at a pH of about 9 to 10 or higher, however, resulted in hydrolysis of the crystal and formation of $ZrO_2$.

EXAMPLE 100

Solid zirconium 2-bromethyl phosphonate was slurried in an aqueous solution of 2-carboxyethyl phosphonic acid, a trace (1% mol) of HF was added and the mixture refluxed overnight. The infrared spectrum of the solid after this period definitely showed the presence of the carboxylic acid carbonyl band at 1710 $cm^{-1}$. The X-ray powder pattern of the exchanged product was virtually identical to the starting material. This was likely due to the fact that zirconium 2-bromoethyl phosphonate has an interlayer spacing of 13.0 Å and the 2-carboxy analog 12.8 Å. Based on stoichiometry, about 5 to 10 percent of the sites were exchanged. This being more than the apparent surface site, interlamellar exchange took place.

EXAMPLE 101

An aqueous solution of organic compounds for use in sorption experiments was prepared by shaking 25 ml of chloroform, 25 ml of toluene and 25 ml of hexane in a separatory funnel with 100 ml of deionized water for ten minutes. After settling for five minutes, the aqueous layer was separated and stored in a stoppered flask.

A gas chromatographic analysis of the aqueous solution yielded peaks for ethanol (a stabilizer present in the chloroform reagent used), chloroform and water. The ratio of chloroform peak area to ethanol peak area was determined for two samples at 15 minute intervals prior to beginning the sorption experiment.

A 3.060 g portion of a tetravalent metal organophosphate was added to the aqueous solution, the stopper replaced, and the mixture agitated briefly. After 15 minutes, a sample was withdrawn for gas chromatographic analysis. The mixture was agitated, then allowed to settle for about five minutes prior to obtaining each of the remaining samples in the experiment.

Ethanol was not extracted from the solution in a significant amount. However, more than 50 percent of the chloroform was extracted by the compound. This indicates the utility as a selective sorbent which removes specific contaminants from solutions, while leaving other dissolved materials in solution.

The above procedures of Examples 87–101 are illustrative of simple utility screening tests which can be used to show ways of using the solid compounds of the invention whether crystalline, semicrystalline, or amorphous. Of course, the tests are preferably modified by the skilled chemist to suit the fundamental character of A loading curve was obtained for the solution of zirconium 2-carboxyethyl phosphonate. The loading curve was prepared by plotting the pH of the solution versus the milli equivalents of copper extracted per gram of zirconium 2-carboxyethyl phosphonate. The loading curve is shown in FIG. 11 by the curve designated as semicrystalline.

EXAMPLE 88

The ion exchange capability of the product in Example 49 was demonstrated for both the sulfonic acid and sodium sulfonate forms of that compound.

A 0.50 g portion of the acid form was slurried with 10 ml of 0.215 N copper sulfate solution. The pH of the solution was initially 3.80 but immediately dropped to 0.92 the initially white solid became a pale blue color, and the blue solution color decreased markedly in intensity. Atomic absorption analysis of the solution after exchange indicated a copper concentration of 0.093 N, for copper loading in the solid of 2.46 meq/g, or 77 percent of the theoretical capacity.

The exchange experiment was repeated with the sodium sulfonate form of the compound. After exchange, the solution had a pH of 2.88 and a copper content of 0.135 N. Loading of the solid was calculated as 1.62 meq/g, or 51 percent of the theoretical capacity.

EXAMPLE 89

The mixed component product of Example 18 was shown to be very selective in its complexative absorption of amines by virtue of the ten carbon cross-links from one layer to the next. This behavior is a form of "molecular sieving."

In four separate experiments the behavior of two —OH containing zirconium phosphate layered solids toward two different amines was investigated. The two amines were a bulky trioctylamine and a small ethylamine. As the table below indicates, the noncross-linked zirconium phosphate picked up both amines from a methanolic solution. However, the product of Example 18 picked up only the small amine, due to the constricting effect of the bridging ten carbon groups.

Absorption of Amines

| Solid | Amine | Molar Ratio of Amine/-OH Group in Product |
|---|---|---|
| $Zr(O_3P-OH)_2$ | $C_2H_5NH_2$ | 0.86 |
| $Zr(O_3P-OH)_2$ | $(C_8H_{17})_3N$ | 0.24 |
| $Zr(O_3P(CH_2)_{10}PO_3)_{1/3}(O_3POH)_{4/3}$ | $C_2H_5NH_2$ | 0.31 |
| $Zr(O_3P(CH_2)_{10}PO_3)_{1/3}(O_3POH)_{4/3}$ | $(C_8H_{17})_3N$ | 0.00 |

EXAMPLE 90

Extraction of palladium +2 ion from aqueous solution by ion exchange with $Zr(O_3P\phi)_{8/5}(O_3PCH_2CH_2CO_2H)_{2/5}$.

A solution of palladium (II) chloride was prepared by dissolving about 1.0 g of commercially available palladium (II) chloride in about 100 ml of water under a nitrogen purge. A small amount of undissolved material was removed by filtration. The pH of this solution was 2.90. To this solution was added 3.0 g of $Zr(O_3P\phi)_{8/5}(O_3PCH_2CH_2CO_2H)_{2/5}$. The pH decreased to 2.35. Using an auto-titrator in a pH stat mode, the pH was raised in small steps to 3.5 by addition of 0.10 N aqueous sodium hydroxide. The pale yellow solid product was isolated by filtration and washed successively with water, acetone and ethyl ether. After oven drying, elemental analysis indicated 3.72% Pd content of the solid phase.

This example demonstrates the extraction of a precious metal, more broadly a Group VIII metal, from solution. The palladium-containing product incorporates a catalytically active species and represents a novel example of a heterogenized or anchored catalyst which can be used for the reactions shown in the J. C. Bailar and Hartley & Vezey publications incorporated herein.

EXAMPLE 91

In an experiment to determine the ability of zirconium bis(mercaptomethylphosphonate) to extract silver ions from solution, 0.076 g of the compound prepared in Example 29 was shaken in a vial with 5 ml of 0.10 M silver nitrate. The mixture was allowed to stand for several days, after which a sample of the supernatant liquid was decanted for analysis.

The original silver solution contained 10.8 g/l silver and the "extracted" solution was found to contain 4.96 g/l silver, indicating that 5.85 g/l silver was extracted by the compound.

EXAMPLE 92

An experiment was performed to determine the ability of a layered cyano end terminated polymer to extract copper ions from aqueous solution. A 0.09 g portion of the zirconium bis (2-cyanoethylphosphate) compound which was prepared in Example 38 was mixed with 5 ml of a solution containing $0.1MCuSO_4$, $0.5MCH_3COONa$ and $0.5MCH_3COOH$. The mixture was permitted to stand for a day and a portion of the supernatant liquid was decanted and analyzed for copper.

The initial copper solution contained 6.45 g/l Cu and the "extracted" solution contained 5.94 g/l Cu, indicating an extraction of 0.51 g/l copper.

EXAMPLE 93

The experiment of Example 92 was repeated using 0.091 g of the compound and 5 ml of unbuffered 0.1 M $CuSO_4$ solution.

Analyses of the initial copper solution gave a value of 6.33 g/l Cu, and the "extracted" solution contained 5.89 g/l Cu, indicating an extraction of 0.44 g/l copper.

EXAMPLE 94

An experiment to determine the ability of zirconium bis(2-cyanoethylphosphate) to extract silver ions from aqueous solution was performed. A 0.090 g portion of the compound prepared in Example 37 was mixed with 5 ml of 0.1 M $AgNO_3$ solution, allowed to stand for several days and a portion of the liquid decanted for analysis.

The initial silver solution contained 10.8 g/l Ag and the "extracted" solution contained 9.82 g/l Ag showing an extraction of 0.98 g/l Ag.

EXAMPLE 95

Esterification of zirconium 3-carboxypropylphosphonate with n-butanol.

To 100 ml three-necked flask was charged 5.0 g of zirconium 3-carboxypropylphosphate, 40 g n-butanol and 10 g $H_2O$. To this was added 3 ml of HCl as cata-

What is claimed is:

1. A solid polymeric compound having basic structural units of the formula:

$$M(O_3ZO_xR)_n$$

in which M is one or more tetravalent metals, Z is a pentavalent atom selected from the group consisting of phosphorus, arsenic, antimony, vanadium, niobium and tantalum, R is an organo group selected from acyclic and heteroacyclic groups, x is 0 or 1, and n is 2, provided that n is 1 when R is terminated with a tri- or tetra-oxy pentavalent atom.

2. A compound, as claimed in claim 1, in which at least one R is an acyclic group selected from the group consisting of a straight chain or branched alkyl, alkenyl or alkynyl group, either unsubstituted or substituted with one or more of the oxy, thio, halo, oxo, hydroxy, carbonyl, carboxy, carbonyloxy, mercapto, sulfinyl, sulfonyl, imino, amino, cyano, nitro, hydroxyamino, nitroso, cycloalkyl, aryl, aralkyl, aryloxy, arylalkoxy, arylthio, aralkylthio, arylamino, or aralkylamino groups.

3. A compound, as claimed in claim 1, in which at least one R is a heteroacyclic group selected from the group consisting of a branched or straight chain, saturated or unsaturated acyclic group containing one or more of the heteroatoms oxygen, nitrogen or sulfur in the chain, which can be substituted with one or more of the halo, hydroxy, carbonyl, mercapto, sulfinyl, sulfonyl, imino, amino, cyano, nitro, hydroxyamino, nitroso, aryl, aryloxy, arylthio, and arylamino groups.

4. A solid compound as claimed in claim 1, having basic structural units of the formula:

$$M(O_3ZO_xR)_n$$

in which M is at least one tetravalent metal;

Z is a pentavalent atom selected from the group consisting of phosphorus, arsenic, antimony, vanadium, niobium and tantalum;

R is an organo group selected from acyclic and heteroacyclic groups, when R is an acyclic group, the acyclic group has from 1 to about 22 carbon atoms, which can be substituted with one or more of the following constituents: halo, carboxy, aldo, keto, phenyl, cyano, mercapto, nitro, thio, amino, oxy, sulfo, hydroxy, cyclo having from 3 to about 6 carbon atoms, phosphonate, phosphate, phosphine, phosphinoxo, oxyphenyl, heterocyclics having from about 2 to about 11 carbon atoms and having at least one nitrogen, oxygen or sulfur atom in the heterocyclic ring, or phenyl which is substituted with one or more of the above constituents, when R is a heteroacyclic group the heteroacyclic group has from about 2 to about 22 carbon atoms and includes from 1 to about 3 heteroatoms of nitrogen, oxygen or sulfur;

in which x is 0 or 1; and n is 2, provided that n is 1 when R is terminated with a tri- or tetra-oxy pentavalent atom.

5. A compound as claimed in claim 1 wherein the pentavalent atom is phosphorus.

6. A compound as claimed in claim 5 wherein the pentavalent atom is arsenic.

7. A compound as claimed in claim 1 wherein the tetravalent metal is selected from the group consisting of titanium, zirconium, molybdenum, tin, cerium, hafnium, lead, thorium and uranium.

8. A compound as claimed in claim 7 wherein the tetravalent metal is zirconium.

9. A compound as claimed in claim 1 in which an acid group of the formula $$(HO_3ZO_x)$$

is present in the structure as a diluent.

10. A compound, as claimed in claim 5, having basic structural units of the formula:

$$M(O_3PORCOOH)_2$$

11. A compound as claimed in claim 5 having basic structural units of the formula:

$$M(O_3PORSO_3H)_2$$

12. A compound as claimed in claim 5 having basic structural units of the formula:

$$M(O_3PORCN)_2$$

13. A compound as claimed in claim 5 having basic structural units of the formula:

$$M(O_{d\,3}PORSH)_2$$

14. A compound as claimed in claim 3 wherein a heteroatom is sulfur.

15. A compound as claimed in claim 3 wherein a heteroatom is oxygen.

16. A compound as claimed in claim 2 providing layer bridging organo groups containing structural units of the formula:

$$M(O_3ZO_xRO_xZO_3)$$

17. A compound as claimed in claim 1 further comprising from about 0.01 to about 10 percent by weight of a Group VIII metal.

18. A compound as claimed in claim 17 wherein a Group VIII metal is palladium.

19. The use of the compound of claim 1 for catalysis.

20. The use of the compound of claim 1 for sorption of organic compounds.

21. The use of the compound of claim 1 for ion exchange.

22. The use of the compound of claim 1 for ion complexing.

23. The use of the compound of claim 1 for formulating a controlled release composition.

24. The use of the compound of claim 1 as an additive to a polymeric composition.

25. A process for producing the compound of claim 1 which comprises reacting, in a liquid medium, at least one acid compound having the formula $$[(HO)_2OZO_x]_kR$$

wherein k is 1 when n is 2 and k is 2 when n is 1, with at least one tetravalent metal ion to precipitate a solid in which the molar ratio of pentavalent atom to tetravalent metal is about 2 to 1, the pentavalent atom is covalently bonded to R, and R is linked to the tetravalent metal through oxygen.

26. A process as claimed in claim 25 for producing phosphorus containing organo substituted inorganic compounds, which comprises reacting, in a liquid medium, at least one organophosphorus acid compound of the formula $$[(HO)_2OPO_x]_kR$$

with at least one tetravalent metal ion to precipitate a solid in which the molar ratio of phosphorus to tetravalent metal is about 2 to 1, R is covalently bonded to phosphorus, and phosphorus is linked to the tetravalent metal through oxygen.

27. A process as claimed in claim 26 for producing phosphonate compounds, wherein the organophosphorus acid compound comprises at least one phosphonic acid compound of the formula $$[(HO)_2OP]_kR$$

28. A process as claimed in claim 26 for producing phosphate compounds, wherein the organophosphorus acid compound comprises at least one monoester of phosphoric acid having the formula $$[(HO)_2OPO]_kR$$

* * * * *